(12) United States Patent
Cooperman

(10) Patent No.: US 8,865,767 B2
(45) Date of Patent: Oct. 21, 2014

(54) NUTRITIONAL SUPPLEMENT COMPOSITION PROMOTING, INCREASE, DEVELOPMENT, ELEVATION AND ACTIVATION OF "SEROTONIN"

(76) Inventor: Sheila M Cooperman, Boca Raton, FL (US)

(*) Notice: Subject to any disclaimer, the term of this patent is extended or adjusted under 35 U.S.C. 154(b) by 473 days.

(21) Appl. No.: 13/199,385

(22) Filed: Aug. 29, 2011

(65) Prior Publication Data
US 2012/0061280 A1  Mar. 15, 2012

Related U.S. Application Data

(60) Provisional application No. 61/402,473, filed on Aug. 31, 2010.

(51) Int. Cl.
| | | |
|---|---|---|
| *A61K 33/10* | (2006.01) | |
| *A61P 25/24* | (2006.01) | |
| *A23L 1/302* | (2006.01) | |
| *A23L 1/30* | (2006.01) | |
| *A61K 31/51* | (2006.01) | |
| *A61K 31/4415* | (2006.01) | |
| *A23L 1/304* | (2006.01) | |
| *A61K 31/455* | (2006.01) | |
| *A61K 31/202* | (2006.01) | |
| *A61K 31/525* | (2006.01) | |

(52) U.S. Cl.
CPC ............. *A23L 1/3008* (2013.01); *A23L 1/302* (2013.01); *A61K 31/51* (2013.01); *A61K 31/4415* (2013.01); *A23L 1/304* (2013.01); *A23V 2002/00* (2013.01); *A61K 31/455* (2013.01); *A61K 31/202* (2013.01); *A61K 31/525* (2013.01)

USPC ............ 514/560; 424/400; 424/687; 424/600

(58) Field of Classification Search
USPC ........................... 514/560; 424/400, 687, 600
See application file for complete search history.

(56) References Cited

U.S. PATENT DOCUMENTS

2008/0152725 A1* 6/2008 Giordano et al. ............. 424/638

FOREIGN PATENT DOCUMENTS

WO    WO 2008103370    *    8/2008

* cited by examiner

*Primary Examiner* — Sreeni Padmanabhan
*Assistant Examiner* — Sahar Javanmard

(57) ABSTRACT

A Nutritional Supplement Composition promoting the increase, development, elevation and activation of the brain chemical "serotonin" in the "subjects" brain chemistry to improve mood, thought, emotions and, mental stability and functioning comprised of the constituents, Omega 3, Omega 6, Calcium Magnesium, and B-complex is described, as well as the method of administration, the usefulness of the present invention, and who would benefit from the administration of this present invention. This Nutritional Supplement composition may be used for all, in "age appropriate" dosages for different age "subjects". This Nutritional Supplement Composition when administered daily will reduce and stabilize the "subjects" depression, anxiety, obsessive- compulsive behaviors stress related and other emotional and mental conditions. The above statement about the embodiment of the present invention will be further explained in more specific detail in the body of the description.

5 Claims, No Drawings

NUTRITIONAL SUPPLEMENT COMPOSITION PROMOTING, INCREASE, DEVELOPMENT, ELEVATION AND ACTIVATION OF "SEROTONIN"

CROSS REFERENCE TO RELATED APPLICATIONS

Provisional Patent was submitted on Aug. 27, 2010.
The filing date or 37© Date was Aug. 31, 2010.
Provisional Application number-61/402,473
A patent search was conducted. After reviewing over 3000, patents, none were found that even remotely resembled an embodiment claiming to increase the level of the brain chemical "serotonin." In addition none of the embodiments reviewed utilized these particular nutritional supplement constituents or composition for any purpose in the embodiment of the invention
Inventor: Sheila M Cooperman
(Boca Raton, Fla.)
No assignee,
Provisional patent filed Aug. 31, 2010
application number, 61/402,473

BACKGROUND OF THE INVENTION

1. Field of the Invention

It is critical to have good mental health in your life. Millions of people in the world suffer with cognitive, emotional and mental health conditions. The embodiment of the present invention relates to the ability of a particular nutritional supplement composition, when administered daily to children, adolescents, and adults has shown to have a huge positive effect on their levels of "serotonin" as evidenced by the epic improvement in their behavioral and cognitive conditions.

BRIEF SUMMARY OF THE INVENTION

The embodiment of this present invention is comprised of Omega 3, calcium/magnesium and B-complex. It is a nutritional supplement composition used to increase, develop, elevate and activate the brain chemical "serotonin." The "subjects" that have started used this nutritional composition, with a daily dosage for longer than one week, but short as one day for some "subjects" have reported it helped regulate, and stabilize their emotional and mental conditions related to depression, anxiety, obsessive traits times of high-stress, feeling overwhelmed and insomnia as well as other related emotional conditions.

When the embodiment of this present nutritional supplement invention is taken daily, as a maintenance source, it is reported that feelings, of depression, anxiety, obsessive traits as well as related emotional conditions, continue to dissipate, and no longer become problematic.

BRIEF DESCRIPTION OF THE DRAWINGS

There are no figures that accompany the embodiment of the present invention.

DETAILED DESCRIPTION OF THE INVENTION

The foregoing descriptions specifically embody the present invention and are presented for the purposes of illustration and description, and are not appended to limit the invention to the precise forms disclosed and obviously modifications and variations may become possible in the future.

It is very evident that our society has an increasing problem among both the adult population, adolescent and child population with increasing rates of anxiety, depression, obsessive-compulsive behaviors and other emotional and mental health related conditions. Anxiety and depression can lead to a litany of health problems and behavior issues, such as poor self-esteem, body image, overall decreased energy, motivation, substance use, and poor daily functioning. It is often difficult for these individuals to moderate their brain chemistry, to eliminate or alleviate the symptoms of their condition.

Emotional and mental stability plays a critical role in people at all times during their life. Prescription medications of pharmacological content prescribed by medical professionals which claim to improve mental and emotional functioning have often been the only option. These are often prescribed to individuals during stressful and traumatic times and for others during their routine lifetime.

Good mental functioning is paramount in our life, yet it can be one of the most fragile systems in the human body. Specifically, balanced brain chemistry is universally necessary to function in a healthy manner. The increased need for proper brain chemical levels is known by the term (chemical unbalance) and is seen in millions of individuals within our society. This can be during times of stress, unexpected trauma or for some individual's part of their everyday routine functioning. Many individuals suffer with depression, anxiety, obsessive-compulsive disorder as well as severe anger, uncontrollable frustration, grief, feeling overwhelmed, and stress, in response to our societal requirements which have become complex, frustrating, very involved, time consuming and problematic for many.

Due to a myriad of environmental factors, and other circumstances the level of mental health issues, depression, anxiety etc. has increased in our society substantially. It appears the fundamental approaches to help depression, anxiety, obsessive-compulsive disorder and other related mental health conditions has been the use of pharmaceutical medication, when a good diet, good exercise program and talk-therapy is not effective. There are millions of people who do not like the idea of taking medication, have tried it and suffered adverse reactions, can't afford it, or just don't believe in this type of philosophy. Thus there is a need for a composition other than pharmaceutical medication to be available to help those individuals who are in need and want help. It is important to help them improve their emotional and mental conditions and gain mental stability to the level they desire, whether it is just during times of trauma, high stress or for everyday functioning.

The person's mind or brain has the self-capacity to modulate these chemicals with the aid of the proper nutritional supplement composition that works as a catalyst that promotes increase, development, elevation, and activation of the "serotonin" in the brain.

The regulation of brain chemicals seems to be a complex interaction of both the nervous system and the mind. Serotonin is the primary brain chemical, which has the strongest effect of an individual's thoughts, as well as regulates their behaviors, including reactions and their proper mental functioning.

The embodiment of my present invention is another alternative to medication in assisting with brain chemical modulation, but unlike medication it is an option, free of side-effects or adverse reactions. Yet ,like pharmaceutical products it must be administered at a maintenance level. It has been reported by "subjects" using this nutritional supplement composition, they have experienced a significant improvement and reduction of their emotional and mental health conditions.

It is understood that the embodiment of the present invention is not limited to the particular methodology or protocols and the like described herein and they may vary. It is also to be understood the terminology used herein is used for the purpose of describing particular embodiments only and not intended to limit the scope of the present invention.

Unless undefined otherwise all technical and scientific terms used herein, have the same meaning as commonly understood by one of the ordinary skilled in the art to which this invention belongs. The methods and materials that are described, although another method and materials similar or equivalent to those described herein could be used in the practice or utility of the present invention all references cited herein are incorporated by referencing herein the embodiment of the present invention in their entirety.

The termed "disease state" as used herein may comprise any state where one or more of the organs or components of an organism can malfunction. The term "disease state" may refer to any deterioration of any component of the body. The term "disease state" may refer to any deficiency that the body presents. This "disease state" can refer to the conditions of depression, anxiety, obsessive-compulsive, lack of anger management, stress related issues, lack of patience, tolerance, lower mental functioning capacity and other emotional issues.

"Disease state" may also comprise disorders associated with addiction, eating disorders, obsessive thoughts and behaviors, insomnia, mood disorders, body self-mutilation, and other self-destructive behaviors. The term "disease state" can therefore refer to both the "physiological" stressful state and the "psychological" stressful state. "Physiological" states can often be a component of the "Psychological" stressful state. Many cognitive and mental health conditions encompass both the "physiological" state and the "psychological" state. Ex. Postpartum pregnancy depression, anorexia, bulimia, premenstrual syndrome, menopause, Peri-menopause The term "subject" is used herein comprises of any and all organisms and includes the term patients. "Subject" will refer to a human both male and female of all ages. Proper balanced brain chemistry is essential for maintaining health of any "subject". Adequate brain chemistry is especially critical during, ex. "physiological" or "psychological" stressful periods. These periods comprise for Ex. pregnancy, fertility issues, post-pregnancy, premenstrual, peri-menopause, addiction, substance recovery, substance withdrawal, post- surgery, grief, bereavement, divorce, job termination, post-service and for a portion of "subjects" everyday routine functioning.

For illustrative purposes the principles are shown by way of example of composition and methods described. In the following description numerous details are set forth to provide an understanding of the examples. It is apparent however, these examples may be practiced without limitation details of content.

It is envisioned that the plurality of nutrients provided including all the vitamins and minerals and other non-active ingredients required for this composition are respective to create the desired results. It is envisioned that this plurality of nutrients was created for the means to increase, develop, elevate and activate the "subjects" serotonin level in their brain.

It is also envisioned that other plurality combination or alternate vitamin, mineral, composition or use of pharm chemicals may not be provided for the same product utility for the purpose of increase, elevation, activation or development of the brain chemical "serotonin" respectively.

Description of the preferred embodiment, best mode for carrying out the invention is presented in terms described. A nutritional supplement composition and delivery method, comprised of nutrients, vitamins and minerals, flavor enhancements, and other inactive ingredients that has the gustatory properties that appeal to the "subject" and when administered on a daily dosage will increase, develop, activate or elevate the levels of serotonin in the brain.

The embodiment of the present invention composition promotes, increase, elevation, activation, and development of "serotonin" when administered daily. It is a maintenance composition comprised of Omega 3, 6, B-complex, calcium magnesium and other non-active compounds that add to the content to create the finished product of the embodiment of the present invention.

Separately the individual constituents in the nutritional supplement composition may aid the human body in other body functioning, however, this nutritional supplement composition in the embodiment of the present invention has the sole purpose for the promotion of the increase, elevation, activation and development of "serotonin" for the direct purpose of alleviating, reducing, modulating, and moderating ones mental, and emotional stability and conditions. The nutritional supplement composition is one link of a complex equation, which assists the "subject" to have the self-capacity to build the necessary level of serotonin.

According to the embodiment of the present invention the daily administration of the nutritional supplement composition results in the increase, elevation, development and activation of serotonin. This continues to create positive feelings, mental stability, and reduction of the distorted and negative thoughts that fuel and accompany depression, anxiety, obsessive-compulsive disorders and other related emotional, mental and trauma related conditions.

The embodiment of the present invention includes the method of increasing the brain chemical serotonin. The embodiment of the present invention includes the nutritional supplement composition comprised of the constituents, Omega, 3,Omega 6, B-complex and calcium/magnesium. The nutritional supplement in the embodiment of the present invention may be administered in an oral dosage, According to the embodiment of the nutritional supplement composition, it may be administered to the "subject" where the recommended serving size is based on the "subjects" individual weight and age. As with all products given to a child under 13 years of age, parent or guardian should first consult with their doctor. For children less than 13 years of age, the nutritional supplement composition in the embodiment of this present invention is appropriate and can be consumed on a daily administration dosage as indicated in claim 2. The embodiment of the nutritional supplement composition maybe be packaged in different dosages in response to the targeted "subject". Parents of young "Subjects" who have been using this nutritional supplement composition have been reporting a significant improvement. For some young "subjects" who suffer with obsessive-compulsive, thoughts, behaviors, and self-mutilating or self-punishing behaviors parents have reported a recent absence of these behaviors since they have been utilizing the embodiment of the present invention.

A nutritional supplement composition with constituents including Eicosapentaenoic Acid (EPA), of about 300 mg, Docosahexaenoic-(DHA), of about 200 mg, B-1 Thiamin, of about 50 mg, B-2 Riboflavin of about 50 mg, B-3 Niacin, of about 50 mg, B-6 Pyridoxine, of about 50 mg Folic Acid, of about 200 mcg, B-9 Biotin, of about 50 mcg, B-12 Cyanocobalamin, of about 50 mcg, Pantothenic acid, of about 50 mg, Calcium citrate and carbonate of about 150 mg, Magnesium oxide of about 150 mg. Other inactive ingredients including effervescent powder, of about 1.5 gm, citric acid of about 1.5 gm and variety of fruit flavoring of about 4 gms. This is the children's constituent composition.

A nutritional supplement consisting of Omega 3-Eicosapentaenoic Acid (EPA), of about 360 mg, Docosahexaenoic (DHA), of about 360 mg, B-1 Thiamin, of about 100 mg, B-2 Riboflavin, of about 100 mg, B-3 Niacin, of about 100 mg, B-6 Pyridoxine, of about 100 mg Folic Acid, of about 400 mcg, B-9 Biotin, of about 100 mcg, B-12 cyanocobalamin, of about 100 mcg, Pantothenic acid, of about 100 mg, Calcium citrate and carbonate of about 300 mg, Magnesium oxide of about 300 mg. other inactive ingredients including effervescent powder, citric acid and variety of fruit flavoring. This is the adult constituent composition.

This preferred embodiment is individually foil packed, vacuum sealed for solvency and potency. This embodiment of the present invention is envisioned can take a variety of forms including a pill, tablet, caplet, capsule, chewable tablet, quick dissolve tablet, and effervescent tablet, effervescent powder, hard gelatin capsule, soft gelatin capsule, enteric coated a powder, liquid suspension, gelatin gummy, lozenge, cake, candy food product, nutritional beverages, and confection.

The embodiment of the present invention may be administered before, with or after food, am or pm. It can be administered daily, having the "subject" consuming one sealed pack, each containing one oral dosage of the composition, before, during or after food. The preferred embodiment of the present invention, the nutritional supplement composition will be mixed with water or juice and then consumed. For adults during extreme trying, traumatic, or when experiencing more severe or exacerbating emotional or mental episodes, the "subject" can consume, a dosage twice a day. It can be taken before, with or after eating.

The embodiment of the present invention may be incorporated in other forms not listed without departing from the scope of the present invention. By the way of illustration and not limitation, the constituents may also be poured into juice, another beverage, or incorporated or added into raw food, ex. fruit smoothie, frozen desert, fruit salad, sorbet, ice cream and other desserts or sprinkled over and mixed into other types of foods. The above pre-packed single serving size of the nutritional supplement composition provides the proper amounts of constituents to promote the increase, elevation, activation and development of serotonin.

The composition may include non-active compounds such as buffers, thickeners, flavorings, sweeteners, colorings, effervescence, and other excipients or non-active ingredients known in the art.

According to the embodiment of the present invention, the nutritional supplement can be formulated for a single or double daily administration with no adverse reactions or expected side-effects or toxicity or over consumption. The ingredients in the nutritional supplement are water soluble and there are no negative reactions to consuming these supplements.

The embodiment of the present invention further pertains to therapeutic methods for managing moods, behaviors, and thought-processing during both those "disease states" and in extreme emotional circumstances and also every day functioning for some "subjects". The nutritional supplement can be administered to "subjects" at increased amounts when necessary to moderate the serotonin level in the "subjects" brain.

Some individuals appear to naturally maintain the levels of serotonin, and do not experience the behaviors and emotions that are caused by serotonin decline. The other brain chemicals dopamine and norepinephrine may play a role, but "serotonin" is the primary brain chemical affecting the individual's ability to function well, and modulate mood and their emotional state.

The embodiment of the present invention will create improvement, with maintenance of depression, anxiety, obsessive-compulsive disorders, substance withdrawal, distorted and skewed impressions, surrounding eating disorders, hoarding, body dysmorphic disorder, obsessive ritualistic behaviors etc. It will improve cognitive capacity and help stabilize emotional and cognitive impairment.

Even though not all people suffer with mental health and emotional symptoms, issues and conditions, the using of this embodiment of the present invention for some "subjects" may be to protect mental and cognitive wellness, can be taken as a preventative measure.

*As always, it is important for those "subjects" who are currently diagnosed with extreme, or terminal illness and taking any types of medication to first consult with their medical professional to prevent any type of negative interactions.

While the foregoing is directed to the embodiments of the present invention other and further embodiments of the invention may be devised without departing from the basic scope thereof, and the scope thereof, is determined by the claim that follows.

What is claimed is:

1. A method of treating a mental condition or mood disorder selected from depression, anxiety, and obsessive compulsive disorder in a subject in need thereof, comprising administering a therapeutically effective amount of a nutritional supplement consisting of: eicosapentaenoic acid (EPA) of about 360 mg; docosahexaenoic (DHA) acid of about 360 mg; thiamin-100 mg; riboflavin-100 mg; niacin-100 mg; pyridoxine-100 mg; folic acid-400 mcg; biotin-100 mcg; cyanocobalamin-100 mcg; pantothenic acid-100 mg; calcium citrate-400 mg; magnesium oxide-400 mg; and optionally, effervescent powder or gelatins.

2. The method of claim 1, wherein the nutritional supplement is self-administered daily.

3. The method of claim 1, wherein the nutritional supplement is orally consumed.

4. The method of claim 1, wherein the subject is human.

5. The method of claim 1, wherein the subject is 6 years old and older.

* * * * *

UNITED STATES PATENT AND TRADEMARK OFFICE
CERTIFICATE OF CORRECTION

| | | Page 1 of 1 |
|---|---|---|
| PATENT NO. | : 8,865,767 B2 | |
| APPLICATION NO. | : 13/199385 | |
| DATED | : October 21, 2014 | |
| INVENTOR(S) | : Sheila M Cooperman | |

It is certified that error appears in the above-identified patent and that said Letters Patent is hereby corrected as shown below:

In the Claims

Column 6, line 59, insert:

--6. The method of claim 1, wherein the nutritional supplement is in the form selected from the group consisting of a pill, tablet, caplet, capsule, chewable tablet, quick dissolve tablet, a powder, effervescence tablet, effervescent powder, hard gelatin capsule, soft gelatin capsule, enteric coated, gummy, lozenge, cookie, candy, cake beverage, and dessert.

7. The method of claim 1, wherein the nutritional supplement is in the form of a liquid suspension.--

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 8,865,767 B2
APPLICATION NO. : 13/199385
DATED : October 21, 2014
INVENTOR(S) : Sheila M Cooperman It is certified that error appears in the above-identified patent and that said Letters Patent is hereby corrected as shown below:

On the title page, under abstract "5 Claims, No Drawing Sheets" should read --7 Claims, No Drawing Sheets--

In the Claims

Column 6, line 59, insert:

--6. The method of claim 1, wherein the nutritional supplement is in the form selected from the group consisting of a pill, tablet, caplet, capsule, chewable tablet, quick dissolve tablet, a powder, effervescence tablet, effervescent powder, hard gelatin capsule, soft gelatin capsule, enteric coated, gummy, lozenge, cookie, candy, cake beverage, and dessert.

7. The method of claim 1, wherein the nutritional supplement is in the form of a liquid suspension.--

This certificate supersedes the Certificate of Correction issued December 16, 2014.

Signed and Sealed this
Twenty-fourth Day of March, 2015

Michelle K. Lee
*Director of the United States Patent and Trademark Office*